United States Patent [19]

Williams

[11] 4,298,282
[45] Nov. 3, 1981

[54] GAUGE FOR MEASURING CARPET SOILING

[76] Inventor: Keith Williams, 1820 H St., Fresno, Calif. 93721

[21] Appl. No.: 148,137

[22] Filed: May 9, 1980

[51] Int. Cl.³ .................................... G01N 21/88
[52] U.S. Cl. ................................ 356/237; 356/238; 356/243
[58] Field of Search ............... 356/243, 237, 238, 421, 356/422, 425, 445

[56] References Cited

U.S. PATENT DOCUMENTS 1,802,052  4/1931  Guernsey et al. .................... 356/243

Primary Examiner—Vincent P. McGraw

Attorney, Agent, or Firm—Edgar W. Averill, Jr.

[57] ABSTRACT

A soil gauge for measuring the relative amount of soiling of a carpet. The soil gauge is made from a transparent material having several viewing areas. The viewing areas are covered with a multiplicity of opaque marks in varying degrees of concentration. An unsoiled sample of carpet is placed next to the carpet to be tested and the soil gauge is placed between the unsoiled sample and the user's line of vision. When the appearance of the unsoiled carpet, as viewed through the gauge, is as close in appearance as possible to the soiled carpet, the position along the gauge through which this similar appearance is achieved is noted, and this position is a measurement of the relative soiling of the carpet.

7 Claims, 4 Drawing Figures

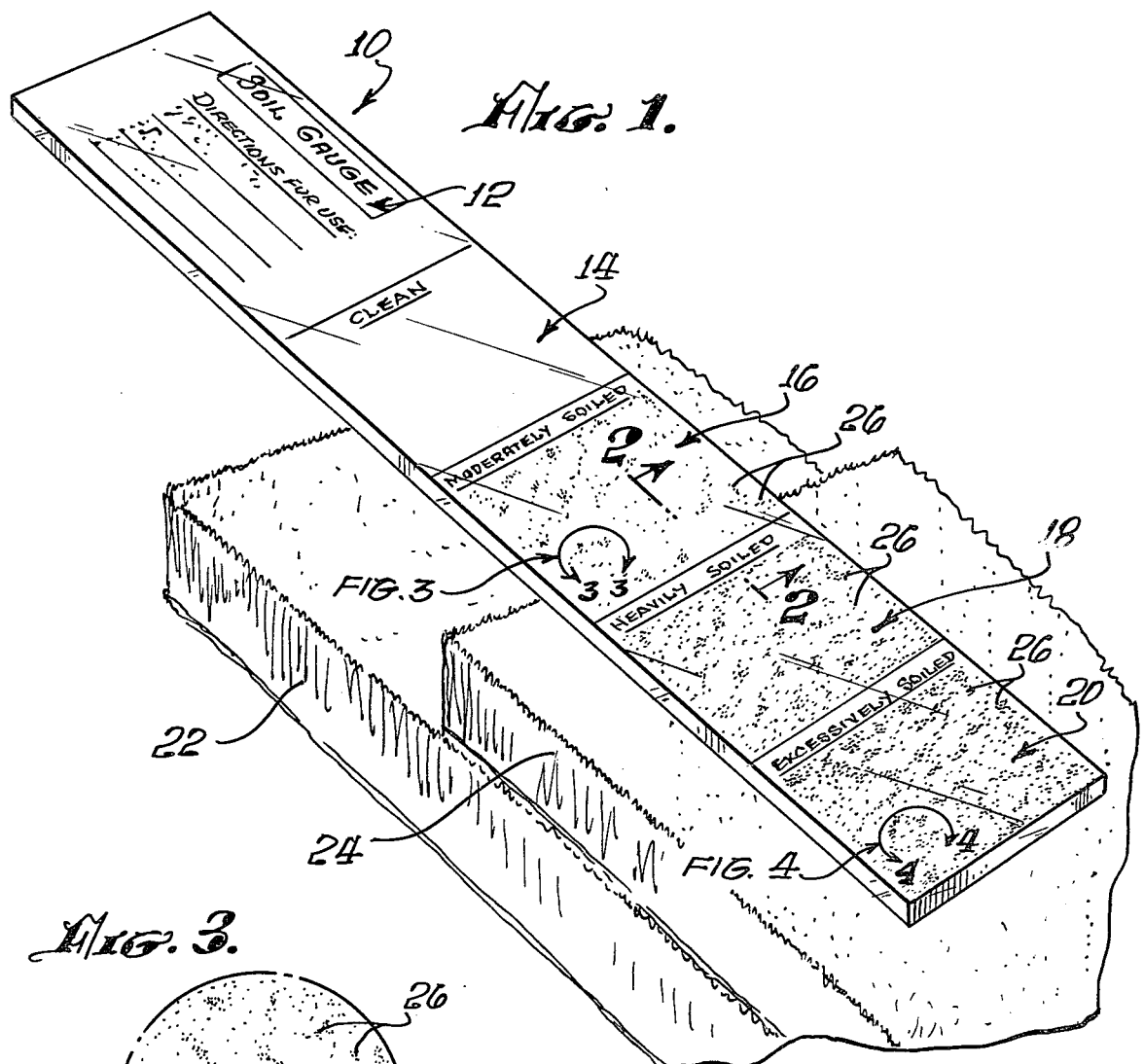
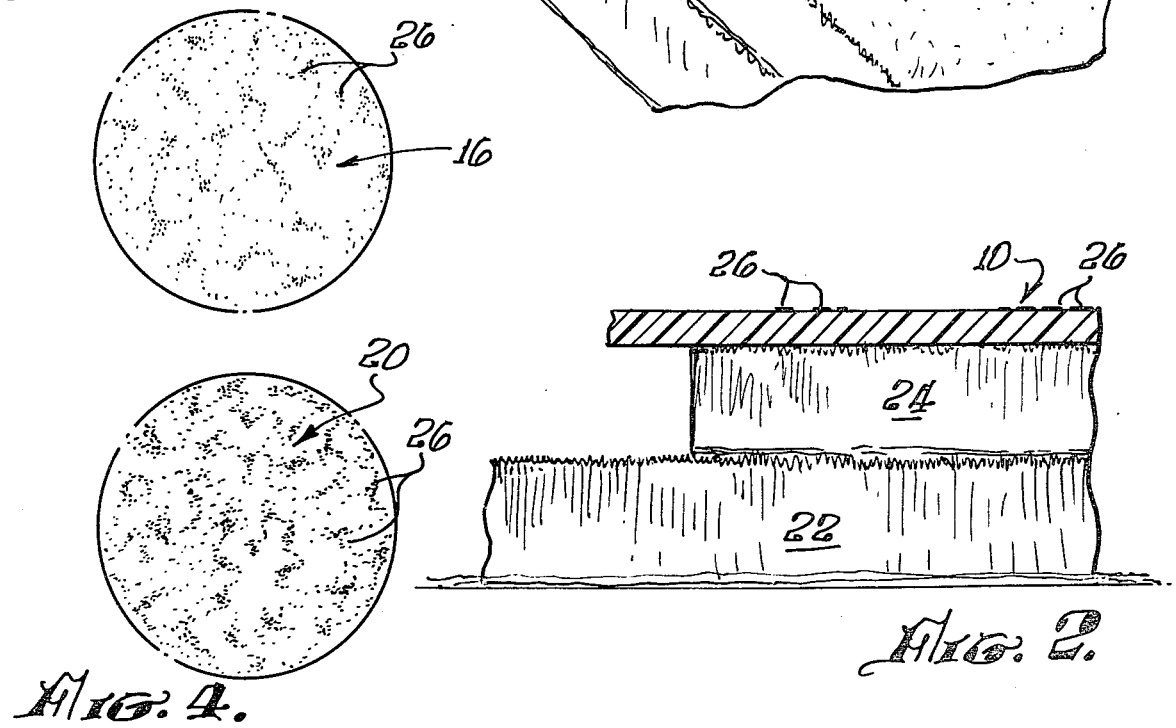

GAUGE FOR MEASURING CARPET SOILING

BACKGROUND OF THE DISCLOSURE

The field of the invention is soil indicators, and the invention relates more particularly to devices or methods for providing an objective measurement of the degree of soiling of carpets. It is important that a carpet be cleaned before the degree of soiling reaches a very high level so that the carpet may be restored to its original appearance by cleaning. If the amount of soiling is excessive, it is usually impossible to return the carpet to a like-new appearance no matter how often it is cleaned. On the other hand if the carpet is cleaned when it is only moderately soiled, it may be brought to a like-new appearance in most instances and maintained for a far longer period of time with such periodic cleaning. It is difficult, however, for the unskilled person to determine the time or amount of soiling at which the carpet should be cleaned. Laboratory testing utilizing reflectance measurements with a double beam recording spectrophotometer have been run to determine the time or amount of soiling at which the carpet should be cleaned. Laboratory testing utilizing reflectance measurements with a double beam recording spectrophotometer have been run to determine the degree of soiling at which level professional carpet cleaning may restore the carpet to a like-new appearance. It is, of course, impractical to run such test in the average home or office, and there is thus a need for a portable and inexpensive soil gauge which will approximate the results achieved with reflectance measurements utilizing a spectrophotometer.

SUMMARY OF THE INVENTION

It is thus an object of the present invention to provide a portable and inexpensive soil gauge for determining the degree of soiling of carpet.

The present invention is for a gauge and the method of using the same. The gauge measures the relative amount of soiling of a carpet and comprises a transparent strip having a plurality of viewing areas located thereon. At least one of the viewing areas is covered with a multiplicity of small opaque marks positioned on the strip with an adjacent viewing area, the position along the strip at which the appearance of the unsoiled carpet viewed through the strip is as close as possible to the appearance of the soiled carpet provides a measurement of the relative soiling of the carpet. The method of the present invention thus comprises placing a sample of unsoiled carpet adjacent to a sample of soiled carpet and viewing the unsoiled carpet through a transparent strip having graduated amount of small opaque marks thereon. The unsoiled carpet is viewed through the strip until the appearance of the unsoiled carpet is closest to that of the soiled carpet. The position on the strip at which the appearance is closest is a measurement of the relative degree of soiling of the soiled carpet.

BRIEF DESCRIPTION OF THE DRAWINGS

FIG. 1 is a perspective view of the gauge of the present invention positioned over a sample of unsoiled carpet which has been placed over a sample of soiled carpet.

FIG. 2 is an enlarged cross-sectional side elevation taken along line 2—2 of FIG. 1.

FIG. 3 is an enlarged plan view of a portion of the gauge of FIG. 1.

FIG. 4 is an enlarged plan view of a portion of a gauge of FIG. 1.

DESCRIPTION OF THE PREFERRED EMBODIMENTS

The soil gauge of the present invention is shown in perspective view in FIG. 1 and indicated generally by reference character 10. Soil gauge 10 has four discreet viewing areas indicated by reference characters 14, 16, 18 and 20. Soil gauge 10 is fabricated from a transparent strip of material such as an acrylic plastic or glass. A plastic material is preferred because of its resistance to breakage and printability. Area 14 is marked with the word "clean" and has no opaque marks 26 printed thereon. In contrast, area 16 has a concentration of opaque dots or squiggles that are random in configuration and in distribution. These opaque marks are shown best in enlarged view in FIG. 3 and in side view in FIG. 2. It has been found, surprisingly, that by providing a multiplicity of opaque marks that it is possible to obtain a good correlation between reflectance measurements made on a double beam recording spectrophotometer, and the appearance of pieces of unsoiled carpet viewed through the gauge adjacent the pieces of soiled carpets. The same correlation was not found when a smoke-colored piece of transparent plastic was used in place of the sample of clear plastic with multiplicity of marks printed thereon. Even more surprising is the observation that opaque marks which are not completely uniform in size or not completely uniform in distribution correlate far more accurately with apparent soiling than evenly spaced dots of the same size of the type commonly utilized in printing and referred to as a "screen." Thus, a multiplicity of randomly spaced opaque marks is the preferred embodiment of the present invention. The marks should be opaqued and should block at least ninety percent of the light reflected on them.

The instructions for use of the soil gauge are printed on gauge 10 and indicated at area 12 of the gauge. To use the gauge to provide an objective measure of the amount or degree of soiling of soiled carpet 22, a sample of unsoiled carpet 24 is placed adjacent or on top of the soiled carpet 22. The gauge 10 is positioned so that the unsoiled carpet 24 is seen through the four viewing areas 14, 16, 18 and 20 of gauge 10. The user then selects which of the four viewing areas is closest in appearance to the soiled carpet. This viewing area then tells the user the degree of soiling as "clean," "moderately soiled," "heavily soiled" or "excessively soiled."

In use, if a carpet is not cleaned, it will progress from its original new appearance to a heavily soiled appearance. It is possible to arbitrarily select different stages of this soiling process and these stages are referred to herein as "excessively soiled," "heavily soiled," and "moderately soiled." An experienced carpet cleaner will realize that "soiling" involves a subjective judgment and after many years of dealing with carpet cleaning, persons become quite expert in rating the degree of soiling of carpeting. The terms "moderately soiled," "heavily soiled" and "excessively soiled" have been chosen arbitrarily to refer to three stages of soiling which require different steps by the owner to return the carpet to a like-new appearance. If the carpet is "moderately soiled," the consumer would be instructed either to clean the traffic areas of the carpet with an approved do-it-yourself product or have a professional cleaner come and clean the traffic area. If the carpet appears to be "heavily soiled", the consumer would be instructed to have a professional carpet cleaner come in and do a thorough cleaning of the carpet. If the carpet is "excessively soiled," the consumer would be instructed that he or she could not expect the carpet to ever be cleaned to satisfactorily and that the use of the carpet has exceeded the purpose for which it was intended. These three terms are roughly equivalent to the following drops in reflectance values as made in a laboratory using a double beam (G.E. type) recording spectrophotometer:

Moderately Soiled 10%–15%
Heavily Soiled 15%–25%
Excessively Soiled 30%–40%

The "clean" viewing area 14 is, of course, not marked. The viewing areas should have between 5% and 50% of the viewing surface covered with opaque marks. Preferably, the "moderately soiled" viewing area 16 should have between 10% and 15% of its surface covered, the "heavily soiled" viewing area 18 should have between 15% and 25% of its surface covered and the "excessively soiled" viewing area 20 should have between 30% and 40% of its surface covered.

Based on tristimulus measurements, a good correlation has been found between the reflective measurements and the degree of soil (Brightness=100Y) as long as a "screen" is used that permits the transmittance of the dominant wave length (coordinates x and y). The "purity" of the hue changes with the screen as it does also with the factor of actual soil, since the type of soil will vary depending upon the geographical area in which the carpet is located together with the type of soil which is commonly tracked into the carpeted area. With the gauge of the present invention, excellent correlation has been found with the various different types of soil and with various types of carpets.

It should be noted that actual particulate soil will be removed with routine of vacuuming, and the binding soil requiring cleaning is generally oily in nature. The oily soil when combined with other soils is opaque and dark appearing, and it is believed that this is why the use of dark, opaque dots or squiggles results in a close correlation with the actual soil appearance of the carpet.

It has been found important that there be ummarked or clear areas in the soil gauge between the opaque marks so that the dominant wave length may be allowed to pass through the gauge.

Various field tests were run using a photovolt reflectometer having a green tristimulus filter, and the percentage drop in reflectance in areas which an experienced porfessional carpet cleaner rated as moderate, heavy and excessive is shown in the table below:

| Color | Type | Fiber | % Drop in Reflectometer Reading Moderate | % Drop in Reflectometer Reading Heavy | % Drop in Reflectometer Reading Excessive |
|---|---|---|---|---|---|
| White | Loop Pile | Wool | 11 | 21 | 33 |
| Gold | Cut Pile | Nylon | 18 | 27 | 36 |
| Beige Tweed | Loop Pile | Nylon | 14 | 25 | 45 |
| Dark Orange | Shag Cut | Nylon | 14 | 23 | 43 |
| Dark Blue | Pile | Nylon | 12 | 28 | 41 |

A second measurement was made on the same samples utilizing a comparison against a perfect reflecting standard for the four carpets of soiling for soiling rated as "moderate," "heavy" and "excessive" by an experienced carpet cleaner.

| Color | Type | Fiber | % Drop in Reflectometer Reading Moderate | % Drop in Reflectometer Reading Heavy | % Drop in Reflectometer Reading Excessive |
|---|---|---|---|---|---|
| White | Loop Pile | Wool | 8 | 22 | 37 |
| Gold | Cut Pile | Nylon | 13 | 22 | 36 |
| Beige Tweed | Loop Pile | Nylon | 15 | 27 | 40 |
| Dark Orange | Shag Cut | Nylon | 16 | 28 | 38 |
| Dark Blue | Pile | Nylon | 14 | 21 | 43 |

Field measurements were also conducted and areas of carpet considered moderately, heavily and excessively soiled were located where possible and the drop in reflectometer reading utilizing a green tristimulus filter are shown in the table below:

| Color | Type | Fiber | % Drop in Reflectometer Reading Moderate | % Drop in Reflectometer Reading Heavy | % Drop in Reflectometer Reading Excessive |
|---|---|---|---|---|---|
| Gold Tweed | Loop Pile | Olefin | 11 | 23 | — |
| Green Tweed | Loop & Cut Needle | Nylon Nylon Olefin | 10 | — | — |
| Rust | Punch Loop & | Hair | 13 | 21 | 34 |
| Red | Cut | Nylon | 12 | 25 | — |
| Dark Brown | Loop Loop | Acrylic | 17 | 27 | 40 |
| Brown | Pile Cut | Olefin | 8 | 23 | 38 |
| Beige | Pile Loop | Wool | 10 | 23 | — |
| Gold Beige Tweed | Pile Loop Pile | Nylon Nylon | 13 8 | 23 21 | 35 — |
| Gold Tweed | Loop Pile Loop | Nylon | 12 | 20 | 32 |
| Orange | Pile Loop | Nylon | 9 | 24 | — |
| Gray | Pile Loop | Olefin | 8 | 18 | 30 |
| Rust | Pile Loop | Olefin | 15 | 24 | 39 |
| Gold | Pile Loop | Olefin | 10 | 21 | 34 |
| Red | Pile Cut | Olefin | 13 | 25 | 37 |
| White | Pile | Wool | 11 | 20 | 27 |

It is preferable that the transparent portion of the soil gauge be as close to perfect transparency as possible and if the transparency is less that about 90%, then the gauge does not correlate well with observed amounts of soiling. While it is preferred that the gauge be fabricated from a transparent material with opaque marks thereon, it is possible to make a soil gauge utilizing an opaque material with irregularly shaped openings passing therethrough somewhat similar to a window screen. That is, where the term "transparent strip" is used in the claims, it is possible to substitute an opening although it is believed to be more economical to place the opaque marks on a transparent member.

The type of screen or markings used to indicate the soiled areas is not of critical importance and any number of screening methods or sizes and shapes of marks may be used. It is important, however, that there be clear areas to allow the passage of the dominant wave length and therefore fine screens such as those below about 32.5 line is not generally satisfactory.

Darker colored carpets show a lesser degree of change even though the amount of soiling is the same as in the lighter colored carpets. The soil gauge also reflects this lesser degree of change and darker colored carpets do show less soil and do appear easier to clean than lighter colored carpets. Thus, the soil gauge of the present invention will provide an aid to the carpet purchaser when soiling is a major consideration. The purchaser will be able to view various samples of carpet through different portions of the soil gauge and note the difference in appearance resulting therefrom.

The marks may be printed on the upper surface as shown in FIG. 2, lower surface or laminated in the middle of the transparent strip. Instead of discreet viewing areas, the amount of mark coverage could gradually increase along the gauge and indicia such as the letters A through F could be printed on the gauge.

The present embodiments of the invention are thus to be considered in all respects as illustrative and not restrictive, the scope of the invention being indicated by the appended claims rather than by the foregoing description. All changes which come within the meaning and range of equivalency of the claims therefore are intended to be embraced therein.

What is claimed is:

1. A soil gauge for measuring the relative amount of soiling of a carpet, said soil gauge comprising:
   a transparent strip;
   a plurality of viewing areas located in said strip, at least one of said viewing areas being covered with a multiplicity of small opaque marks positioned in said viewing area with adjacent viewing areas having an increasing coverage whereby when a sample of unsoiled carpet is viewed through one of said viewing areas and matched with the sample of soiled carpet, a relative measurement of degree of soiling is obtained.

2. The soil gauge of claim 1 wherein said opaque marks are randomly spaced.

3. The soil gauge of claim 1 wherein said opaque marks cover between 5% and 50% of the viewing surface of the transparent strip.

4. The soil gauge of claim 1 wherein said opaque marks are located in discreet viewing areas, each of said viewing areas having about the same degree of mark coverage and adjacent viewing areas have an increasing degree of coverage.

5. The soil gauge of claim 4 wherein the marks are located in three viewing areas.

6. The soil gauge of claim 5 wherein said first viewing area has a mark coverage of between 10% and 15%, said second area has a mark coverage of between 15% and 25% and said third area has a mark coverage of between 30% and 40%.

7. A method for obtaining an objective measurement of the degree of soiling of a carpet, said method comprising the steps of:
   placing the sample of unsoiled carpet adjacent a sample of soiled carpet;
   viewing the unsoiled carpet through a transparent strip having a graduated amount of spaced opaque marks thereon;
   viewing a portion of the soiled carpet adjacent the sample of unsoiled carpet viewed through said transparent strip;
   moving said transparent strip until the appearance of the unsoiled carpet is closest to the appearance of the soiled carpet; and
   noting the position along the strip adjacent the portion of said strip which appears closest in appearance to the soiled carpet.

* * * * *